United States Patent [19]
Shillington et al.

[11] Patent Number: 6,024,216
[45] Date of Patent: *Feb. 15, 2000

[54] DISPOSABLE CONTAINER WITH SELF-LOCKING CLOSURE

[75] Inventors: Randall S. Shillington, Carlsbad; David R. Millar, Orange; Rex O. Bare, Lake Forrest, all of Calif.

[73] Assignee: Med-Safe Systems, Inc., Oceanside, Calif.

[*] Notice: This patent issued on a continued prosecution application filed under 37 CFR 1.53(d), and is subject to the twenty year patent term provisions of 35 U.S.C. 154(a)(2).

[21] Appl. No.: 09/061,630

[22] Filed: Apr. 16, 1998

[51] Int. Cl.[7] .................................................. B65D 85/24
[52] U.S. Cl. ............................................ 206/366; 206/1.5
[58] Field of Search ................................. 206/366, 365, 206/1.5, 369, 806; 220/908.3

[56] References Cited

U.S. PATENT DOCUMENTS

| 4,982,843 | 1/1991 | Jones ........................................ 206/366 |
| 5,046,614 | 9/1991 | Torres et al. ............................. 206/366 |
| 5,415,315 | 5/1995 | Ramirez ............................... 206/366 X |
| 5,560,512 | 10/1996 | Hahn ................................... 206/366 X |

*Primary Examiner*—Jacob K. Ackun
*Attorney, Agent, or Firm*—Baker & Maxham

[57] ABSTRACT

A self locking disposable container, comprises a generally box like enclosed container having a top with a limited access opening for receiving medical sharps, a closure mounted within the container and moveable from a normally open position enabling passage of articles through the access opening to a closed position preventing passage of articles through the access opening, and a locking device within the container associated with the closure for latching the closure in the closed position.

20 Claims, 4 Drawing Sheets

DISPOSABLE CONTAINER WITH SELF-LOCKING CLOSURE

BACKGROUND OF THE INVENTION

The present invention relates to sharps disposable containers and pertains particularly to an improved disposable container having an automatic self locking closure.

A huge volume of hypodermic needles are used daily in the medical and health care industry and must be disposed of safely. These used needles pose a major health problem to the medical personnel using them as well as others who may come into contact with them. The safe and effective disposal of these hypodermic needles poses one of the greatest health and disposal problems for the medical and health care industry.

Hypodermic needles are widely used for both injection of medication and for withdrawing blood samples for diagnostic purposes. In many cases the needle is removed from the holder and separately disposed of. In some cases, particularly certain blood drawing devices, the holder is reused. In these cases, it is essential that the needle be easily, quickly and safely removed and safely disposed without risk to the user and others.

A great number of disposable sharps containers have been developed over the years in a effort to provide secure containers for the safe disposable of medical waste and sharps. Many of these are effective when properly and securely closed and disposed of. However, most of these require the conscious active closure and locking of the container by a responsible person. Such responsible person is not always available for securing and disposing of the containers at the appropriate time. Therefore, there is an evident need for a disposable container that automatically closes and locks under certain conditions.

It is desirable that a simple, safe and effective automatic closure for disposable containers be available.

SUMMARY OF THE INVENTION

It is the primary object of the present invention to provide a simple, safe and effective automatic closure for disposable containers.

A self locking disposable container, comprises an enclosed container having a top with a limited access opening for receiving medical sharps, a closure mounted within said container and moveable from a normally open position enabling passage of articles through said access opening into said container to a closed position preventing passage of articles through said access opening, and locking means within said container associated with said closure for locking said closure in the closed position.

BRIEF DESCRIPTION OF THE PREFERRED EMBODIMENTS

The above and other objects and advantages of the present invention will become apparent from the following description when read in conjunction with the accompanying drawings wherein.

DETAILED DESCRIPTION OF THE PREFERRED EMBODIMENTS

Figure 1:
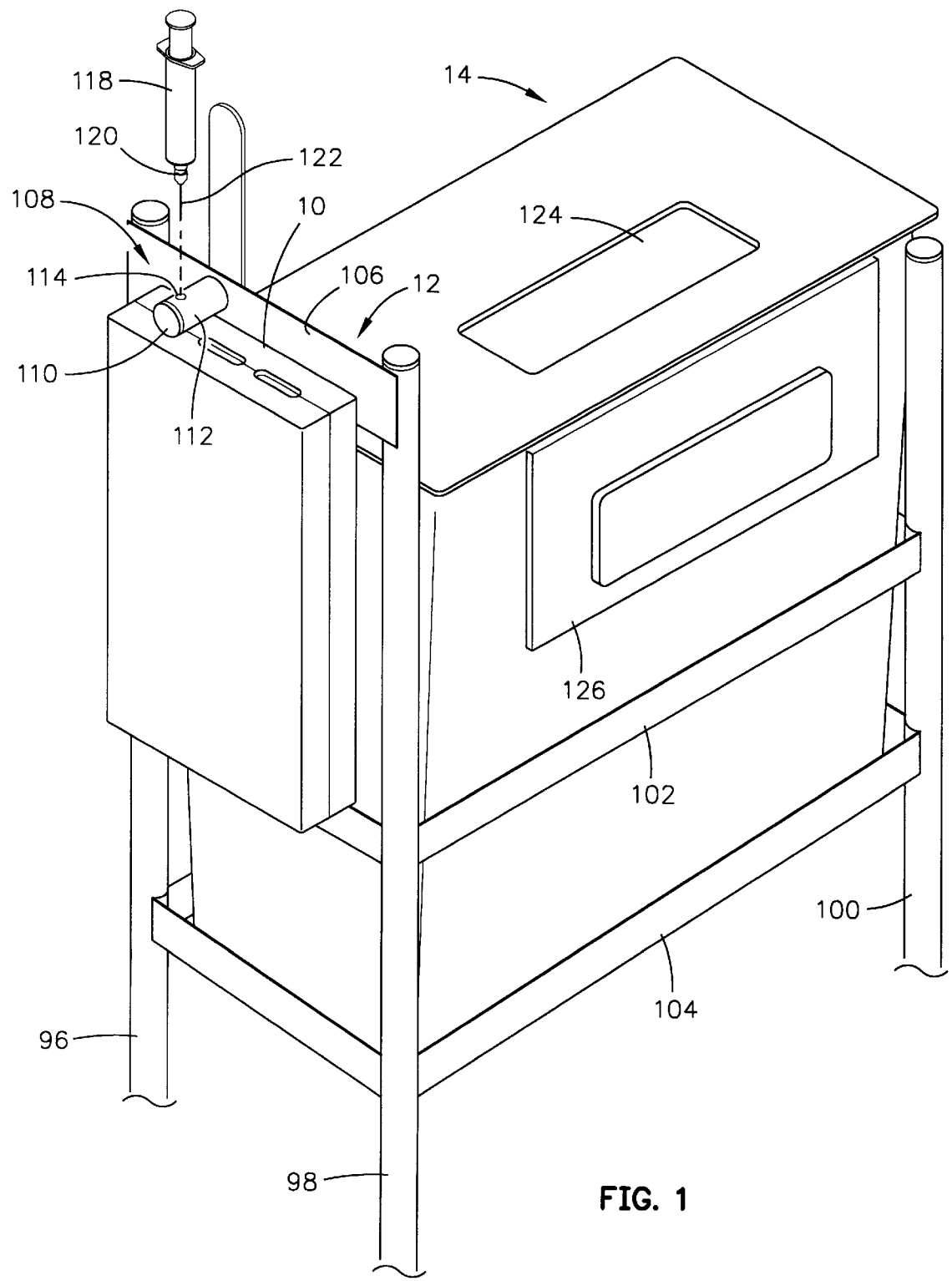
FIG. 1 is a perspective view of an exemplary embodiment of the present invention in combination with a mounting bracket and a disposable syringe container.

Referring now to the drawings, and particularly to FIG. 1, there is illustrated an exemplary embodiment of a disposable sharps container embodying a closure assembly in accordance with the invention designated generally by the numeral 10. The sharps container 10 is shown mounted on and in combination with a mounting bracket designated generally at 12 on which is mounted a disposable syringe container designated generally at 14. However, the container may be non-disposable and/or it may be mounted in a lockable housing.

The illustrated embodiment of present invention is directed to a disposable sharps container wherein the container closure automatically closes and locks upon the occurrence of a certain event such as removal from the bracket. It may also be constructed to close upon the reaching of a predetermined fill level, the opening of a cabinet door or other suitable event.

Figure 2:
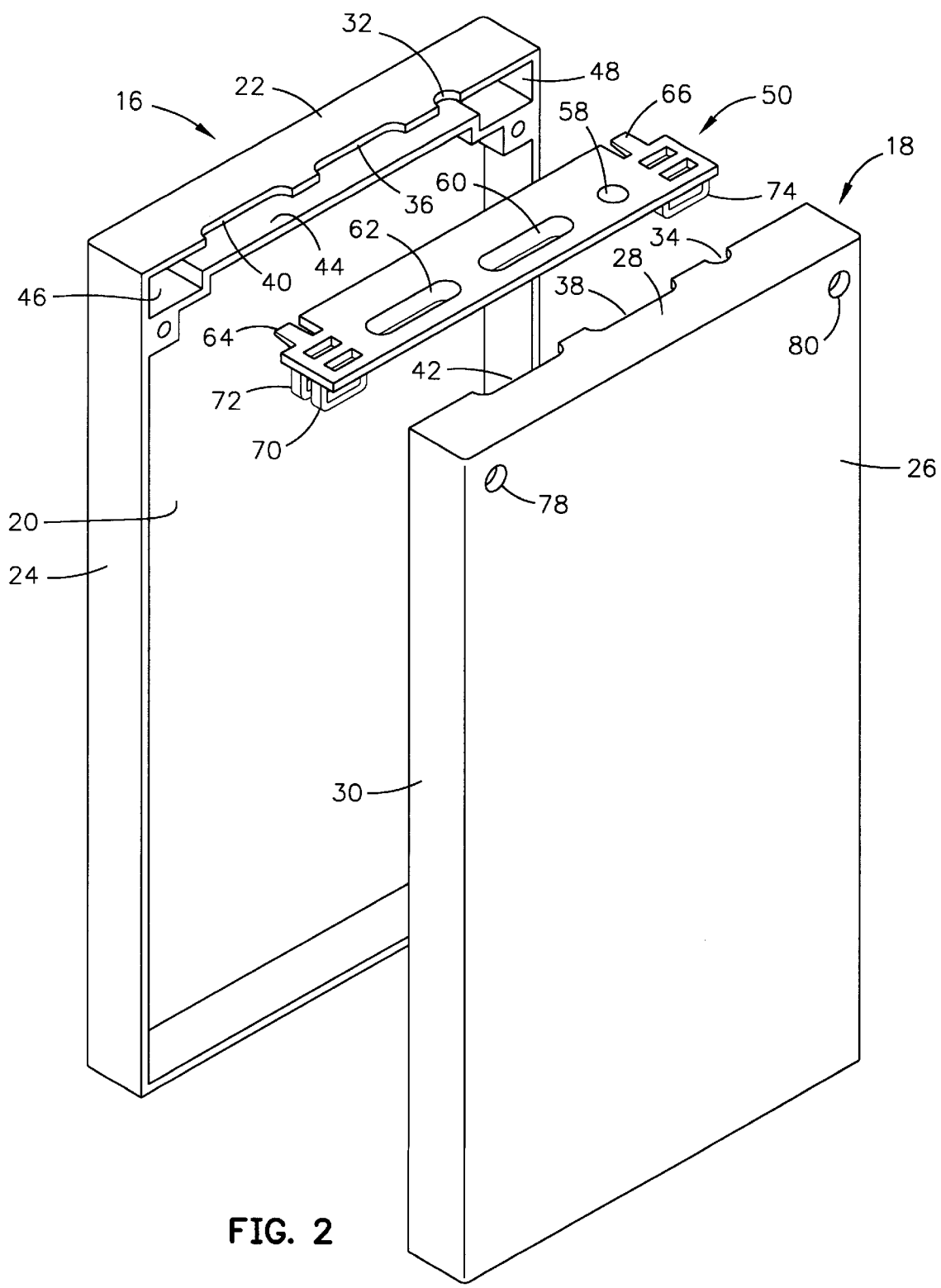
FIG. 2 is a perspective assembly view of the embodiment of FIG. 1.

Referring to FIG. 2, the container may have any shape but, in the illustrated embodiment has a generally rectangular box-like configuration and is formed of two mirror image half shells 16 and 18. However it may be formed such as by molding or the like as a unitary housing with a suitable access opening. The illustrated shell 16 is formed of a rectangular back panel 20 with a top panel 22 and peripheral side and bottom wall 24. The shell 18 is similarly formed of a rectangular back panel 26 with a top panel 28 and peripheral side and bottom wall 30. The shells may be constructed of any suitable material but is preferably constructed of a durable plastic such as by molding.

The top panels 22 and 28 are each formed with notches which mate to form a plurality of openings for receipt of needles and other medical sharps. A pair of semi-circular notches 32 and 34 form a circular opening for receipt of needles and needle hubs, as will be further discussed. A second pair of elongated notches 36 and 38 form an elongated opening in which may be located a gear tooth needle removal device as will also be further described. An additional pair of opposed elongated notches 40 and 42 form an additional elongated opening which is adapted to receive other sharp devices and the like. These openings may be formed in any other suitable manner such as being molded in their entirety into a unitary top or other access panel.

The top or opening area of each of the half shells is formed with a stepped shelf or inner panel spaced from the top or outer panel to provide space for a closure panel. Shell 16 has a shelf or inner panel 44 (FIG. 2) spaced below the outer or top panel 22 with end step down portions 46 and 48 providing a guide channel for a slidable closure designated generally by the numeral 50. The panel 26 has a similar spaced shelf 52 (FIG. 3) having end step downs 54 and 56 corresponding to those in the half shell 16. This construction provides a closure assembly with a protected chamber to receive and mount the closure in a protected position totally within the container.

The closure 50 has a generally rectangular planar upper surface with a circular opening 58 which selectively aligns with the opening formed by notches 32 and 34, an elongated slot opening 60 which selectively aligns with the opening formed by notches 36 and 38 and an elongated opening 62 which selectively aligns with the opening formed by notches 40 and 42. When the container is assembled, the closure 50 is captured in an inaccessible position within the container.

Figure 4:
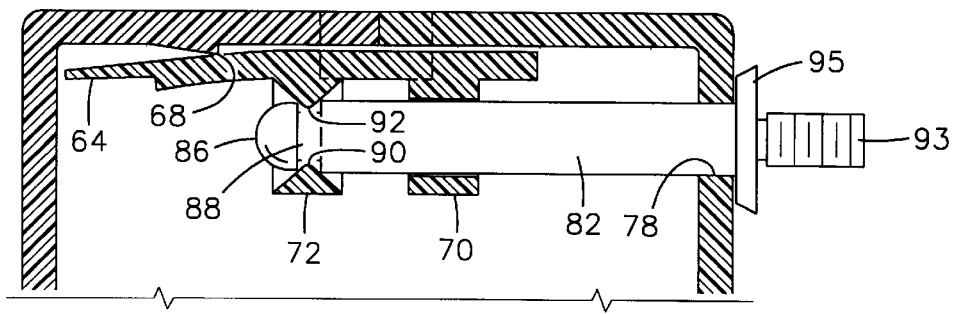
FIG. 4 is a section view taken on line 4—4 of FIG. 3.
Figure 5:
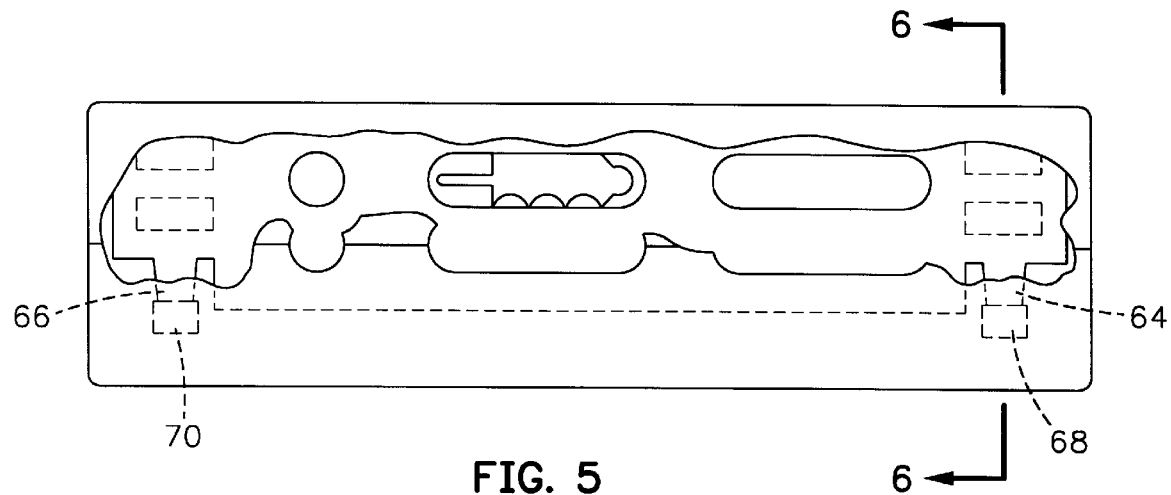
FIG. 5 is a detailed top plan view like FIG. 3 showing the closure in the closed position.
Figure 6:
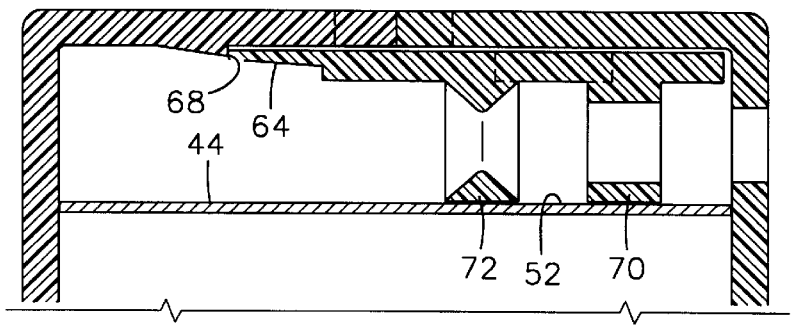
FIG. 6 is a section view taken on line 6—6 of FIG. 5.

The closure is also formed with a pair of latch or locking tabs 64 and 66 (FIG. 5), which engage latch abutments or shoulders 68 and 70, as can be seen in FIGS. 4, 5 and 6. The container is assembled with the latch tabs in an over-riding position, as shown in FIG. 4, with the closure in the open position with its openings aligned with the openings formed in the top of the container. This permits the container to be filled with sharp objects and to be automatically closed and locked in a suitable manner such as will be described. When the closure is moved to the closed position, the locking tabs 64 and 66 spring down into engagement with shoulders 68 and 70 (FIGS. 5 and 6) and lock the closure in the closed position.

Figure 3:
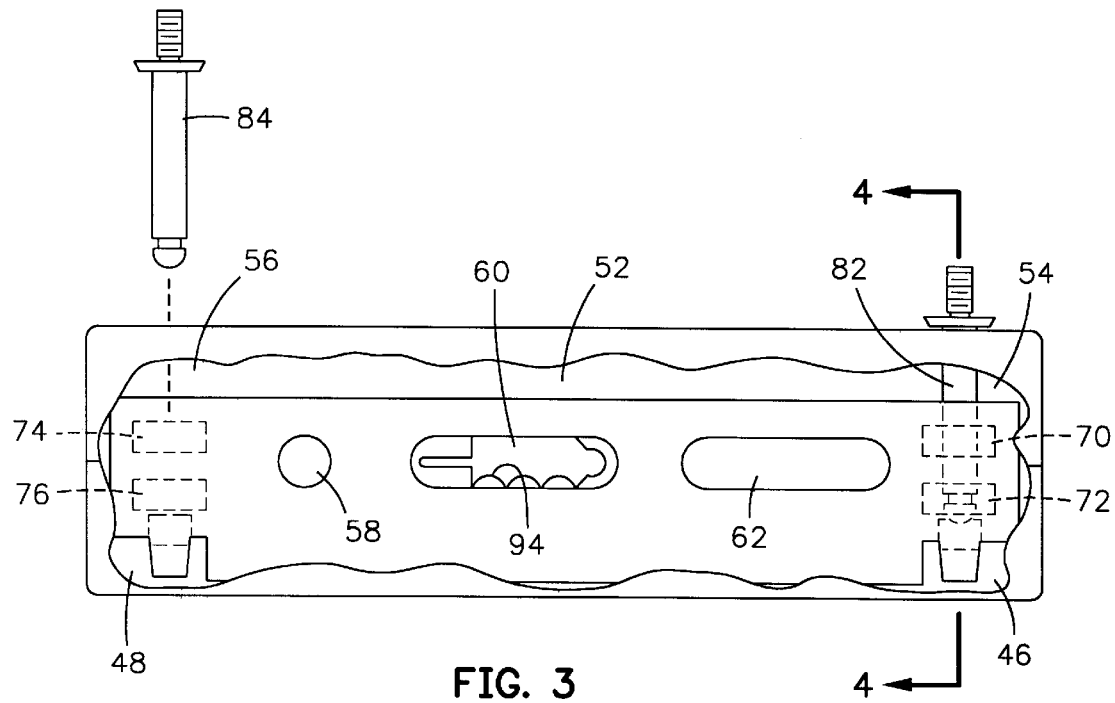
FIG. 3 is a detailed top plan view with portions broken away of the embodiment of FIG. 1 showing the closure in the open position.

As shown in FIGS. 2–4, the enclosure 50 is formed with a pair of loops 70 and 72 on one side of the under surface, and a pair of loops 74 and 76 on the other side of the under surface. These loops, as will be further explained, cooperate with mounting pins for the container which pins will be mounted on a mounting bracket, or the like, to mount the container for normal use. In this embodiment, the pins act to automatically close the container upon removal of the container from the mounting bracket. The loops latch to the pins (FIG. 4) which pull the closure to the closed position.

In assembling the container as shown in FIG. 2, the closure 50 is inserted into the slot in the upper end of one of the half-shells such as 16, and positioned fully forward such that the openings 58, 60 and 62 are aligned with the openings formed in the upper surface or top panels of the half-shells. The half-shells are mated together and bonded along their peripheral edges in a suitable manner to permanently secure them together. Any number of bonding or welding techniques, such as heat welding, sonic welding, chemical welding, and the like, may be utilized. In the initially assembled condition, the closure is in the fully open position such that the container may then be suitably mounted on a support bracket and filled with medical sharps in the usual manner. When the container is removed from the bracket, the closure is automatically closed and locked and cannot be re-opened. However, it will be appreciated that the closure may be in the closed positioned and automatically opened upon mounting to a bracket. Removal from the bracket would then preferably automatically close it permanently.

The half-shell 18 is formed with a pair of thru-bores 78 and 80 at the upper corners thereof for receipt of a pair of mounting pins 82 and 84. The mounting pins 82 and 84 are identical and only one of which, 82, will be described in detail. The pin 82 is formed with an elongated cylindrical body or shank having a rounded outer end or tip 86 and a circular groove 88 adjacent the outer tip. The outer end is adapted to insert into loop 74 which is formed with chamfered inner walls defining inner opposing edges 90 and 92 which extend into and engage and latch to the shoulders formed by the groove 88. This engagement occurs when the container is mounted on a support bracket or the like. Upon removal of the container from the bracket, the closure which is latched to pins 82 and 84 moves with them from the open position, as illustrated in FIGS. 3 and 4, to the closed position as shown in FIGS. 5 and 6. The loops them slip or unlatch from the ends of the pins.

The end of the mounting pin 82 is engaged by the loop 72 and is latched thereto such that movement of the container to the left, as shown in FIG. 4, moves the container but leaves the closure coupled to the mounting pin 82 until the closure moves to the position, as shown in FIG. 6. At this point the edge of the closure engages the wall of the container and enables the pin to be removed from its connection with loops 72 and 76. The pin 82 is formed with a threaded end 93 and radial flange 95 for mounting to a suitable support.

The pins 82 and 84 are formed to latch to the closure so that when the container is moved from the pins, the closure moves to the position shown in FIG. 6, the latch tab 64 falls down and engages shoulder 68 to lock the closure in its closed position. Thus, the closure becomes essentially self-closing and self-locking in the illustrated embodiment. It is apparent that other forms of moving the closure to or from its open or closed position and to its locked position may be utilized. For example, means for latching of it in its open position and releasing it for latching or locking in the closed position may be utilized.

The closure is completely encased within the housing forming one wall of the container such that no access to it for opening it is possible once the closure is locked. Thus, once the closure has been moved to its closed and locked position, access to the interior of the container in any manner is essentially prevented. In addition, the container is essentially fool-proof in its closing and locking, such that it does not require the conscious effort of a user to move the closure to its locked position and assure that it is locked. A simple act of removing the container from the mounting bracket results in the closure moving to the closed and locked position.

The self locking closure in accordance with the present invention may be incorporated in any number of different types of containers such as disclosed in U.S. Pat. No. 5,103,997 of Shillington et al. It may also be used on containers that are placed in lockable housings, and on closures for housings for containers.

Referring to FIGS. 3 and 5, the opening 60 in the closure is formed with a needle removal device with gear-like teeth 94, such as disclosed and claimed in U.S. Pat. No. 5,402,887 granted to Richard Shillington on Apr. 4, 1995. Other types of needle removal devices or slots may also be incorporated in one or more of the openings into or associated with the container.

Referring back to FIG. 1, one embodiment of the container is designed to be used in conjunction with a mounting bracket or stand 12 and a syringe disposable container 14, as illustrated. However, it is to be understood that the self locking closure assembly may be used on containers for any and all disposable articles. A suitable mounting stand, as illustrated, comprises four upstanding legs, only three of which 96, 98 and 100, are shown connected together by frame members 102 and 104. A bar or strap 106 is connected between the upper ends of legs 96 and 98 at one end of the stand and serves to mount a pair of the mounting studs or pins 82 and 84. A syringe needle disabling device designated generally at 108 is mounted on the bar 106 and is adapted to receive needles and the needle sleeve of a syringe and cut them to prevent their re-use, as will be further explained.

The illustrated disabling device comprises a cylindrical shaft 110 on which is relatively rotatably mounted a sleeve 112 with a thru-bore 14 which is disposed over and aligned with opening 58 of the container 10. One of the rod and sleeve 110 and 112 is stationary and the other rotates by means of a lever 116. A syringe 118 to be disabled, has a hub connecting sleeve 120 to which a hub of a needle 122 is connected either by threads or a Luer-lock type connection. The needle and the connecting sleeve 120 of the syringe 118 are inserted into the bore 114 and the handle or lever 116 actuated manually to rotate one of sleeve and shaft 110 and 112 relative to the other. This relative rotation acts to thereby shear the needle hub sleeve from the syringe and also shear the needle in two.

A closure 126 is pivotally mounted on the container 14 to close the opening 124. The syringe is then disabled and not subject to re-use. Similarly, the needle is not only destroyed to prevent its re-use, but also inside the container 10 and inaccessible. The syringe body 118 may then be placed in an opening 124 of container 14. The plastic which makes up the syringe bodies may then be recycled while the needle parts may then be disposed off in the usual manner. The container 14 may be made of any suitable material for disposal.

The self-locking closure, in accordance with the present invention, may take any number of forms and may be embodied in any number of different types of containers. Also, the closure is not limited as to its orientation. It may be oriented horizontally, vertically, or on any angle suitable for the situation.

The invention may be embodied in any number of forms of closure suitable to the application, such as for example, it may be embodied in a movable closure which rotates within an enclosed container and have features as previously described for opening and closing. The movable closure may also take the form of a folding accordion material or may be formed of a flexible thin gauge sliding metal material within the enclosed container. The closure may also be either a tilting or pivoting closure, such as the closures in the Shillington U.S. Pat. No. 5,103,997, as previously mentioned and related closures. Other forms that the closure may take include segmented rolling (tambour) material and molded segmented materials. The closure may also be manufactured as a self-contained unit adaptable for attachment to any number of different containers.

While we have illustrated and described our invention by means of specific embodiments, it is to be understood that numerous changes and modifications may be made therein without departing from the spirit and scope of the invention as defined by the claims.

We claim:

1. A self locking disposable container, comprising:
   an enclosed container having at least one wall having an inner surface and an outer surface and a limited access opening formed in said wall for receiving medical sharps;
   a closure mounted within said container and moveable along said inner surface from a normally open position enabling passage of articles through said access opening to a closed position preventing passage of articles through said access opening;
   a locking member within said container engageable between said container and said closure for locking said closure in the closed position;
   an actuator opening in said container proximate said closure; and
   an actuating member adapted to be inserted in said actuator opening to move said closure to the closed position.

2. An apparatus according to claim 1 wherein said closure has an opening therein, and said opening is aligned with said access opening in said open position and not aligned with said access opening in said closed position.

3. An apparatus according to claim 2 further comprising:
   a mounting bracket for said container; and
   said actuating member is on said mounting bracket and operative to move said closure to said closed position when said container is removed from said mounting bracket.

4. An apparatus according to claim 1 further comprising:
   a mounting bracket for said container; and
   said actuating member is on said mounting bracket and operative to move said closure to said closed position when said container is removed from said mounting bracket.

5. An apparatus according to claim 4 wherein said actuating member comprises a pin engageable with said closure when said container is mounted on said bracket.

6. An apparatus according to claim 5 wherein said pin comprises a shoulder coupling with said closure for moving said closure to said closed position upon movement of said container from said bracket.

7. An apparatus according to claim 6 wherein said locking member comprises tabs on said closure engageable with shoulders within said container when said closure is in said closed position.

8. An apparatus according to claim 7 wherein said shoulder on said pin is engageable with a shoulder on said closure and operative to pull said closure to the closed position as said pin is withdrawn from said container.

9. An apparatus according to claim 6 wherein said shoulder comprises an annular shoulder on said pin engageable with a slot defining a shoulder on said closure and operative to pull said closure to the closed position as said pin is withdrawn from said container.

10. An apparatus according to claim 1 wherein said locking member comprises a tab on one of said container and said closure and a shoulder on the other of said container and said closure, said tab engageable with said shoulder when said closure is in said closed position.

11. A self locking disposable container, comprising:
    a generally box like enclosed container having a top having a limited access opening therein for receiving medical sharps;
    a closure slideably mounted adjacent an inner surface of said top within said container and moveable from a normally open position enabling passage of articles through said access opening to a closed position preventing passage of articles through said access opening;
    a locking member within said container engageable between said closure and said top for locking said closure in the closed position;
    an actuator bore in said container; and
    an actuating member adapted to extend into said actuator bore and actuate said closure to the closed position.

12. An apparatus according to claim 11 further comprising:
    a mounting bracket for detachably mounting said container; and
    said actuating member is on said mounting bracket and operative couple to and move said closure to said closed position when said container is removed from said mounting.

13. An apparatus according to claim 11 wherein said closure has an opening disposed in alignment with said access opening when in said open position and disposed in a non-aligned position with said access opening in said closed position.

14. An apparatus according to claim 11 wherein said locking member comprises a tab on one of said closure and said container and a shoulder on the other of said closure and said container, said tab engageable with said shoulder when said closure is in said closed position.

15. An apparatus according to claim 12 wherein said actuating member comprises a pair of spaced apart pins, said container comprises a pair of said spaced actuating bores, and said pair of spaced apart pins extendable through said spaced bores in said container and engageable with said closure when said container is mounted on said bracket.

16. An apparatus according to claim 15 wherein said pair of spaced apart pins each comprises an annular shoulder engageable with a slot defining a shoulder on said closure and said pins operative to pull said closure to the closed position as said pins are withdrawn from said container.

17. A self locking disposable container, comprising:

a generally box like enclosed container having a top with a limited access opening for receiving medical sharps;

a closure slideably mounted adjacent an inner surface of said top within said container and moveable from a normally open position enabling passage of articles through said access opening to a closed position preventing passage of articles through said access opening;

a locking member within said container between said closure and said top and adapted to lock said closure in the closed position;

a mounting bracket for detachably mounting said container; and an actuating member on said mounting bracket operative to engage and move said closure to said closed position when said container is removed from said mounting bracket.

18. An apparatus according to claim 17 wherein said closure has an opening disposed in alignment with said access opening when in said open position and disposed in a non-aligned position with said access opening in said closed position.

19. An apparatus according to claim 18 wherein said locking member comprises tabs on one of said closure and said container and a shoulder on the other of said closure and said container, said tabs engageable with said shoulders when said closure is in said closed position.

20. An apparatus according to claim 17 wherein:

said mounting bracket comprises a pair of spaced apart pins defining said actuating member extendable through spaced bores in said container and engageable with said closure when said container is mounted on said bracket; and said pins having annular shoulders engageable with a slot defining on said closure and operative to pull said closure to the closed position as said pin is withdrawn from said container.

* * * * *